United States Patent [19]

Lavker et al.

[11] Patent Number: 5,279,969
[45] Date of Patent: Jan. 18, 1994

[54] METHOD OF IDENTIFYING AND MODULATING THE ACTIVITY OF LABEL RETAINING CELLS IN HAIR FOLLICLES FOR DIAGNOSTIC AND THERAPEUTIC PURPOSES

[75] Inventors: Robert M. Lavker, Malvern, Pa.; Tung-Tien Sun, Scarsdale, N.Y.; George Cotsarelis, Upper Darby, Pa.

[73] Assignees: Trustees of Univ. of Penn, Philadelphia, Pa.; New York Univ., New York, N.Y.

[21] Appl. No.: 971,687

[22] Filed: Nov. 4, 1992

Related U.S. Application Data

[63] Continuation of Ser. No. 676,185, Mar. 27, 1991, abandoned.

[51] Int. Cl.$^5$ .............................................. G01N 33/48
[52] U.S. Cl. ...................................... 436/63; 435/29; 424/2
[58] Field of Search ........................... 436/63; 424/2, 9; 435/29

[56] References Cited

U.S. PATENT DOCUMENTS 4,806,476  2/1989  Coons et al. .................... 435/172.2

OTHER PUBLICATIONS

Cotsarelis et al., *J. Invest. Dermol.*, 92(3) (1989a).
Cotsarelis et al., *Cell* 57:201–209 (1989b).
Cotsarelis et al., *Cell* 61:1329–1337 (1990).

*Primary Examiner*—James C. Housel
*Assistant Examiner*—Maureen M. Wallenhorst
*Attorney, Agent, or Firm*—Jane Massey Licata

[57] ABSTRACT

Methods of detecting label retaining cells in self-renewing tissues, such as hair follicle, are provided. Methods of modulating the activity of slow-cycling cells and methods of evaluating the efficacy of agents for modulating the activity of stem cell populations are also provided. Generally, cells are continuously labeled, induced into a proliferative phase by exposure to an agent such as TPA or a cytokine, and then observed in relation to established criteria.

4 Claims, No Drawings

METHOD OF IDENTIFYING AND MODULATING THE ACTIVITY OF LABEL RETAINING CELLS IN HAIR FOLLICLES FOR DIAGNOSTIC AND THERAPEUTIC PURPOSES

This is a continuation of application Ser. No. 676,185, filed Mar. 27, 1991, now abandoned.

FIELD OF THE INVENTION

This invention relates to methods of modulating the activity of stem cell populations and the diagnosis and treatment of conditions such as abnormal hair growth or hair loss and skin cancers which are effected by stem cells. This invention was made in the course of work supported by NIH grants AR39674, EY06769, AR34511 and EY4722. The Government has certain rights in this invention.

BACKGROUND OF THE INVENTION

Stem cells are by definition present in all self-renewing tissues. These cells are believed to be long-lived, have a great potential for cell division and are ultimately responsible for the homeostasis of steady-state tissues. Stem cells rarely incorporate radioisotopes after single pulse labeling indicating that they are normally slow cycling. They can, however, be induced to enter the proliferative pool in response to certain growth stimuli. When stem cells undergo occasional cell division, they give rise to more rapidly proliferating "transient amplifying cells" ("TA") which incorporate a radiolabel such as tritiated thymidine ($^3$H-TdR) after a single exposure.

Stem cells possess many of the following properties: they are relatively undifferentiated, ultrastructurally and biochemically; they have a large proliferative potential and are responsible for the long term maintenance and regeneration of the tissue; they are normally "slow-cycling", presumably to conserve their proliferative potential and to minimize DNA errors that could occur during replication; they can be stimulated to proliferate in response to wounding and to certain growth stimuli; they are often located in close proximity to a population of rapidly proliferating cells corresponding to the transient amplifying cells ("TA") in the scheme of (1) stem cell to (2) TA cell to (3) terminally differentiated cell, and they are usually found in well protected, highly vascularized and innervated areas.

Positive identification of stem cells has been difficult because there are no known immunological or biochemical markers specific for epithelial stem cells. Since they are normally "slow-cycling", they cannot be labeled by single pulse administration of radioactive materials typically used to detect actively proliferating TA cells. It has been found that labeling of stem cells requires continuous labeling for a prolonged period. Once labeled, these slow-cycling cells retain isotope for an extended period of time. Such cells have been termed "label-retaining cells" or "LRCs".

Cotsarelis et al., *J. Invest. Dermol.* 92(3) (1989a) disclose a method to facilitate detection of LRCs based on the ability of slow-cycling cells to be recruited to proliferate in response to hyperplastic stimuli. Alzet TM osmotic minipumps were intraperitoneally implanted in adult SENCAR mice to deliver 20 $\mu$Ci of tritiated thymidine ($^3$-HTdR) per day for 14 days. During this labeling period, 0.01% O-tetradecanoylphorbol 13-acetate (TPA) in petroleum (Pet) was applied topically once daily for 4 days to the right flank. The contralateral side was treated with Pet only. Animals were sacrificed during and after labeling. TPA and Pet treated skin was examined by light microscopy and tissue section autoradiography. It was found that TPA treatment caused marked epidermal and follicular hyperplasia, whereas Pet treated sites did not appear morphologically altered. Fourteen days of continuous $^3$-HTdR resulted in greater that 90% labeling of all nucleated epidermal and follicular epithelial cells in both TPA and Pet treated sites. After 4 weeks, only a small number of cells remained labeled (LRCs). These cells were detected with greater frequency in TPA- vs. Pet-treated epidermis. The most striking concentration of LRCs was found to occur in the follicular epithelium.

Using tritiated thymidine ($^3$H-TdR) labeling, a subpopulation of corneal epithelial basal cells located in the peripheral cornea in a region called the limbus, were identified by Cotsarelis et al., in *Cell* 57:201–209 (1989b). These cells are normally slow-cycling but can be stimulated to proliferate in response to wounding and to administration of TPA. The corneal epithelium appears to represent an exceptional situation. LRCs were detected in the basal layer of limbal epithelium. No such cells were detected in central corneal epithelium. It was found that limbal epithelium can be selectively stimulated to proliferate by introducing a wound 1–2 mm away in the central corneal epithelium. Preferential stimulation of limbal epithelial proliferation was also observed when TPA was topically applied to the anterior surface of the eye. It was therefore concluded that the limbal epithelium has a greater proliferative potential than central corneal epithelium.

Label-retaining cells were identified in mouse epidermis by continuously labeling with $^3$H-TdR using subcutaneous injections for seven days. This method labeled almost all epidermal cells. After chasing for four weeks, it was found that a subpopulation of epidermal basal cells maintained labeled-LRCs.

In other experiments, Alzet TM osmotic minipumps were implanted intraperitoneally in mice to deliver $^3$H-TdR for 14 days. Radioactive nuclei of over 95% of corneal epithelial cells and over 80% of limbal epithelial cells was observed. After a four week resting period, all of the radiolabeled cells disappeared from the cornea and few if any could be identified in limbal epithelium, suggesting that LRCs of the corneal-limbal epithelia must have an average cycling time much longer than 14 days and are therefore refractory to labeling under these experimental conditions.

To improve the chances of labeling these stem cells, they were recruited into a proliferative phase by wounding and application of TPA. These experiments showed the existence of a subpopulation of limbal basal cells that are normally slow-cycling but can be induced to proliferate and become labeled after appropriate stimulation.

Stem cells of various epithelia share a common set of features which are summarized in FIG. 7 of Cotsarelis et al.(1989b). The specific location and biological properties of corneal epithelial cells as well as the stem cells of a number of other epithelia including palmar (palm) epithelium, trunk epidermis, hair follicle, dorsal tongue epithelium, and intestinal epithelium are discussed. In FIG. 7(e) it is shown that in hair follicles, the heavily pigmented stem cells are located at the base, in close proximity with follicular papillae and associated vasculature.

In subsequent work, Cotsarelis et al. (1990) show that the hair follicle stem cells were, however, incorrectly identified, Cotsarelis et al. (1989b). In fact, label-retaining cells were found to exist exclusively in the midportion of the follicle at the arrector pili muscle attachment site termed the "bulge" area of the hair follicle (Cell 61:1329-1337).

DETAILED DESCRIPTION OF THE INVENTION

The inventors recently located the putative stem cells of the hair follicle and the sebaceous gland and epidermis to the bulge region of the hair follicle. Using autoradiographic techniques designed to detect slow-cycling cells (label-retaining cells; LRCs), it was surprisingly found that there were very few LRCs in the epidermis. Furthermore, when the hair follicle was surveyed, the inventors determined that there were no LRCs in the matrix cells comprising the bulb, which is the region currently thought to contain follicle stem cells. Rather, the inventors determined that there was a subpopulation of LRCs in the upper portion of the follicle in a region known as the "bulge".

The bulge cells possess many stem cell properties. They mark the end of the permanent portion of the hair follicle. They possess a relatively primitive cytoplasm. They are normally slow-cycling but can be stimulated to proliferate by tumor promoter, TPA. Finally, they are located in a physically well protected and well nourished area. The inventors' identification of a population of putative stem cells located exclusively in the bulge area is consistent with their being the long-hypothesized pluripotent stem cells, giving rise not only to the hair follicle, but also the sebaceous gland and epidermis.

The bulge is a subpopulation of outer root sheath cells located in the midportion of the follicle at the arrector pili muscle attachment site. The prior art taught that hair follicle stem cells reside in the matrix or lower bulb area of the hair bulb. The inventors' discovery provided insight into hair cycle control and the involvement of hair follicle stem cells in skin carcinogenesis and led to the development of methods for identifying and modulating the activity of slow-cycling cells for diagnostic and therapeutic purposes and for evaluating the efficacy of agents for modulating the activity of identified stem cell populations.

One of the most distinguishing features of stem cells is their slow-cycling nature. A single pulse of a radioisotope such as $^3$H-TdR will not label stem cells; labeling requires repeated administration of the isotope for a prolonged period of time. Once labeled, cells that cycle slowly retain isotope for an extended period of time.

A discrete population of mouse hair follicle cells has been identified. These cells are slow-cycling but can be induced into the proliferative phase in response to hyperproliferative stimuli. The location of these cells was unexpected. The stem cells were not found in the matrix area of the bulb where follicular stem cells are currently thought to reside. Rather, the cells were identified in a specific area of the outer root sheath, the bulge. The bulge structure is not unique to the hair follicles of the mouse. Outer root sheath bulges are also found in human hair follicles, as well as trunk and neck skin. The bulge area has attracted so little attention by prior art workers that it is rarely even mentioned in histology 1.ext books. The realization that hair follicle stem cells may reside in the bulge area has provided new insights to the inventors into how the hair cycle is regulated and the involvement of hair follicles in skin carcinogenesis.

THE IDENTIFICATION OF SLOW-CYCLING CELLS IN HAIR FOLLICLES

Twice daily subcutaneous injections of $^3$H-TdR were given to newborn mice over the first seven days of life resulting in labeling of almost 100% of nuclei in mouse epidermis, hair follicles, sebaceous glands, fibroblasts, and endothelial cells. Following a four week resting period ("chase"), no LRCs were identified in the matrix area of the hair follicles indicating that matrix does not contain slow-cycling cells. Unexpectedly, groups of LRCs were found in midfollicle, in the bulge region.

In another set of experiments, adult mice were implanted with Alzet TM osmotic minipumps continuously delivering $^3$H-TdR for two weeks. After a four week chase period, LRCs were found exclusively in the bulge region.

Upon application of TPA, normally slow-cycling cells within adult bulges were stimulated to proliferate. Once the external stimulation was removed, the bulge cells were apparently the only ones that returned to their previously slow-cycling state, retaining their label for a long period of time.

THE BULGE ACTIVATION THEORY

The hair cycle involves three distinct phases: anagen (growing), catagen (regressing), and telogen (resting). The inventors have discovered a new understanding of how the hair cycle is controlled. The bulge stem cells are activated by dermal papilla during late telogen. This is termed "bulge activation". The dermal papilla are activated by the matrix during mid-anagen. Matrix cells are in fact TA cells; therefore, contrary to the teachings of the prior art, matrix cells have a limited proliferative potential. The upward movement of dermal papilla is important for the activation of hair stem cells. Defects in an of these elements could result in abnormal hair growth or hair loss.

In addition, it has been found that stem cells of the hair follicle, rather than interfollicular epidermis, are involved in and are largely responsible for experimental tumor formation in mouse skin.

Cytokines have been determined by the inventors to be useful for modulating stem cell activity. Tumor Necrosis Factor, TNF, has been shown to have widely disparate effects on epithelial proliferation. In the case of cytotoxic dermatoses (graft vs. host disease), TNF can be cytotoxic to rapidly proliferating epithelial cells. Similarly, TNF has been demonstrated to have antiproliferative effects on keratinocyte cultures. However, because keratinocytes in culture are generally hyperproliferative, these studies could not differentiate whether TNF affects slow cycling (stem cells) or normally cycling (TA) cells. Conversely, in inflammatory dermatoses (delayed hypersensitivity reaction) TNF liberated by mast cells may have a secondary effect which enhances epithelial proliferation. For example, TNF induces the expression of ELAM-1 on dermal post-capillary venules, which facilitates the entry of leukocytes into the tissue. These leukocytes in turn liberate a vast number of cytokines, many of which are known to enhance epithelial proliferation.

Cytokines of particular interest include:

Tumor Necrosis Factor (TNF)—Resting mast cells are the major preformed source of this cytokine in normal skin. Cellular targets in acute graft versus host disease have been postulated to be keratinocytes with stem cell properties. Because stem cells are normally slow cycling, but proliferate rapidly upon inductive stimulation, they may be attractive targets for cytokines such as TNF.

Epidermal Growth Factor (EGF)—This cytokine has been shown to have broad biological effects. Most significantly, it has the ability to induce the proliferation of basal keratinocytes. Furthermore, it has been shown to support growth during fetal development, and accelerate re-epithelialization during wound healing.

Transforming Growth Factor(TGF)—TGF has been shown to be involved in the regulation of both growth and differentiation of epithelial cells. It is known to stimulate keratinocyte growth in vitro.

Interleukin-1 (IL-1)—IL-1 is known to induce proliferative activity in epidermal cells.

Previous studies of cytokine/proliferative relationships were done on purified populations of isolated cells. The following experiments using organ culture and relevant in vivo models are designed to assess cytokine effects on epithelial proliferation within the context of an intact microenvironment.

LOCALIZATION OF CYTOKINE RECEPTORS

In studies designed to determine the localization of receptors for cytokines, biotinylated cytokines are added to explants of murine skin in the range of 0.5-50 ng/ml. Tissues are incubated with cytokines for 60 minutes, rinsed thoroughly, and then incubated in medium alone for 10 minutes. Immunohistochemical localization of the cytokine is accomplished using a sensitive avidin biotin immunoperoxidase or immunoalkaline phosphatase stain in accordance with standard techniques.

EFFECT OF CYTOKINES ON SLOW CYCLING CELLS

In studies designed to determine the effects of cytokines on various proliferative cell populations, selected cytokines are added to explants of murine skin. Explant cultures are serially harvested at daily intervals for the first 4 days of exposure, and cytokine effects on $^3$H-TdR incorporation assessed in accordance with standard techniques.

In another series of experiments, a cohort of mice is continuously labeled for 2 weeks with $^3$H-TdR and then allowed to rest for 4 weeks. Once labeled, cells which cycle slowly retain the isotope for an extended period of time and are thus identified as label retaining cells. Cytokines are introduced via intradermal injection to continuously labeled/chased animals. Four hours prior to sacrifice, colcemide (4 mg/kg) is injected intraperitoneally. Animals are sacrificed at 2, 6, 12 and 24 hours after cytokine injection and skin from injected areas fixed and processed for autoradiography according to routine procedures. Appearance of labeled mitotic figures indicates that slow cycling cells have been induced to proliferate.

Methods of evaluating the efficacy of agents for modulating the activity of stem cell populations are provided. Methods of the invention comprise exposing cells to an agent to be tested; continuously labeling said test cells with a selected radiolabel for a selected period; inducing said test cells into a proliferative phase; observing said test cells for labeling; and comparing the labeling of said test cells with established controls for labeled stem cells. Such methods would be useful for evaluating agents to stimulate hair growth or prevent hair loss, for example. Further, such methods would be useful for identifying agents useful for the treatment o skin cancers.

Methods of modulating the activity of stem cells, for example, stimulating slow-cycling cells to promote tissue growth, are provided. Methods of the invention comprise identifying stem cell populations in selected tissue and inducing said stem cells into a proliferative phase. Such methods would be useful for stimulating hair growth or preventing hair loss. Useful agents for inducing identified stem cells into a proliferative phase include TPA and cytokines. Such agents may be administered either internally or topically, either alone or in combination with a pharmaceutically acceptable carrier.

Methods of detecting slow-cycling cells for diagnostic and therapeutic purposes are also provided. Slow-cycling cells are identified, induced into a proliferative phase with a selected agent, and then are observed to determine their number and/or viability relative to established controls. Useful agents to induce the stem cells into a proliferative phase include TPA and cytokines. Such methods are useful for the diagnosis and treatment of abnormal hair growth or hair loss, for example. In addition, such methods may prove useful for the diagnosis and treatment of skin cancers.

While a number of specific embodiments have been set forth, the present invention is to be limited only in accordance with the following claims.

What is claimed:

1. Method of evaluating the efficacy of agents for modulating the activity of bulge cell populations comprising:
   (a) collecting bulge cells from the midportion of a hair follicle at the arrector pili muscle attachment site;
   (b) exposing said bulge cells to an agent to be evaluated;
   (c) continuously labeling said exposed bulge cells with a selected radioisotope for a selected period;
   (d) inducing said labeled bulge cells into a proliferative phase;
   (e) observing said bulge cells for labeling; and
   (f) comparing the labeling of said bulge cells with established controls for labeled bulge cells.

2. The method of claim 1 wherein said labeled bulge cells are induced into a proliferative phase by exposing said bulge cells to TPA or a cytokine.

3. The method of claim 1 wherein said selected radioisotope is tritiated thymidine.

4. Method of evaluating bulge cells in a sample hair follicle for diagnostic and therapeutic purposes comprising:
   (a) collecting bulge cells from the midportion of said sample hair follicle at the arrector pili muscle attachment site;
   (b) continuously labeling said bulge cells for a selected period;
   (c) inducing said labeled bulge cells into a proliferative phase by exposure to TPA or a cytokine for a selected period; and
   (d) observing said bulge cells for labeling to determine the number and viability of said bulge cells relative to established controls.

* * * * *